US012690830B2

(12) United States Patent
Schmidt et al.

(10) Patent No.: US 12,690,830 B2
(45) Date of Patent: Jul. 28, 2026

(54) COMPUTER-IMPLEMENTED METHOD FOR OPERATING AN X-RAY DEVICE, AND X-RAY DEVICE

(71) Applicant: Siemens Healthineers AG, Forchheim (DE)

(72) Inventors: Stefan Schmidt, Stoernstein (DE); Michael Meyer, Hausen (DE); Michael Poellath, Ebnath (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 169 days.

(21) Appl. No.: 18/455,135

(22) Filed: Aug. 24, 2023

(65) Prior Publication Data

US 2024/0065657 A1 Feb. 29, 2024

(30) Foreign Application Priority Data

Aug. 25, 2022 (EP) .................................... 22192175

(51) Int. Cl.
*A61B 6/00* (2006.01)

(52) U.S. Cl.
CPC .......... *A61B 6/4452* (2013.01); *A61B 6/4441* (2013.01); *A61B 6/5211* (2013.01); *A61B 6/54* (2013.01)

(58) Field of Classification Search
CPC . A61B 6/44452; A61B 6/4441; A61B 6/5211; A61B 6/54
See application file for complete search history.

(56) References Cited

U.S. PATENT DOCUMENTS

| | | | |
|---|---|---|---|
| 5,040,203 A | 8/1991 | Janssen et al. | |
| 6,309,102 B1 | 10/2001 | Stenfors | |
| 6,379,041 B1 * | 4/2002 | Schuetz ................. | A61B 6/583 |
| | | | 378/205 |
| 6,582,120 B2 * | 6/2003 | Schomberg .......... | A61B 6/4464 |
| | | | 378/185 |
| 6,764,217 B2 * | 7/2004 | Yasuda .................. | A61B 6/469 |
| | | | 378/205 |
| 6,789,941 B1 * | 9/2004 | Grady .................. | A61B 6/4441 |
| | | | 378/197 |

(Continued)

FOREIGN PATENT DOCUMENTS

| | | |
|---|---|---|
| DE | 69010033 T2 | 1/1995 |
| DE | 19933229 A1 | 3/2000 |

(Continued)

*Primary Examiner* — David J Makiya
(74) *Attorney, Agent, or Firm* — Harness, Dickey & Pierce, P.L.C.

(57) ABSTRACT

An X-ray device has a stand, a support arm, a mount and a C-arm, on which are arranged, opposing one another, an X-ray generator and an X-ray detector. The support arm is coupled to the stand at one end such that it can rotate about a first axis of rotation for the creation of a first degree of freedom of movement and the mount is coupled to the support arm at the other end such that it can rotate about a second axis of rotation for the creation of a second degree of freedom of movement. The first axis of rotation, the second axis of rotation and a central beam of the X-ray generator intersect at one point in all positions of the support arm and of the mount.

18 Claims, 6 Drawing Sheets

(56) References Cited

U.S. PATENT DOCUMENTS

| | | | | |
|---|---|---|---|---|
| 7,634,308 B2 * | 12/2009 | Ogawa | ................... | A61B 6/504 |
| | | | | 378/98.12 |
| 10,751,011 B2 * | 8/2020 | Hou | .................... | A61B 6/4464 |
| 10,827,994 B2 * | 11/2020 | Hou | .................... | A61B 6/4464 |
| 2003/0058996 A1 * | 3/2003 | Graumann | ........... | A61B 6/4233 |
| | | | | 378/196 |
| 2007/0003014 A1 * | 1/2007 | Boese | ................. | A61B 6/4476 |
| | | | | 378/95 |
| 2008/0069309 A1 | 3/2008 | Dorre | | |
| 2015/0036799 A1 * | 2/2015 | Zhang | ................. | A61B 6/4014 |
| | | | | 378/62 |
| 2016/0228080 A1 * | 8/2016 | Margot | ................ | A61B 6/4441 |
| 2018/0279980 A1 | 10/2018 | Barker et al. | | |

FOREIGN PATENT DOCUMENTS

| | | | |
|---|---|---|---|
| DE | 102006043144 A1 | 3/2008 |
| DE | 102018107442 A1 | 10/2018 |
| DE | 202019100924 U1 | 3/2019 |
| EP | 3620110 A1 | 3/2020 |
| WO | WO 2011055741 A1 | 5/2011 |

* cited by examiner

COMPUTER-IMPLEMENTED METHOD FOR OPERATING AN X-RAY DEVICE, AND X-RAY DEVICE

CROSS-REFERENCE TO RELATED APPLICATION(S)

The present application claims priority under 35 U.S.C. § 119 to European Patent Application No. 22192175.2, filed Aug. 25, 2022, the entire contents of which are incorporated herein by reference.

FIELD

One or more example embodiments of the present invention relates to a computer-implemented method for operating an X-ray device for acquiring projection images of an acquisition region of a patient, wherein the X-ray device has a stand, a support arm, a mount and a C-arm, on which are arranged, opposing one another, an X-ray generator and an X-ray detector. One or more example embodiments of the present invention additionally relates to an X-ray device.

RELATED ART

Especially in the field of medical interventions, for example minimally invasive or other interventions, there is a call for X-ray devices which firstly take up little space and disrupt people present as little as possible, but which secondly provide maximum performance, not just as regards the image quality, but also the applications and image acquisition techniques. Thus there is in particular a desire to also be able to perform three-dimensional scans of an acquisition region of the patient using X-ray devices which have an acquisition array that is movable in space and comprises an X-ray generator and an X-ray detector. To this end, projection images of the acquisition region are normally acquired in different acquisition geometries, in particular at different projection angles, by moving to suitable positions with the acquisition array. The projection images can then be used to determine a three-dimensional image dataset of the acquisition region in the form of a computed-tomography image dataset, by employing a reconstruction method. Known reconstruction methods for example comprise filtered backprojection and algebraic/iterative reconstruction techniques.

Another aim in such X-ray devices, besides the corresponding performance, is a compact configuration, in order to minimize obstructions for people in the room, for example during a medical intervention and/or examination, but also to ensure a cost-effective, uncomplicated and low-effort, in particular cost-effective implementation. In the prior art, X-ray devices with a C-arm are mainly known here, on which are arranged the X-ray generator and the X-ray detector opposing one another. In this case the C-arm should be kept as short as possible, in order not to obstruct the personnel. However, this means that for example for a 3D scan from the headside position, in other words when a C-arm is arranged in the longitudinal direction of the patient behind the patient's head, wherein then the longitudinal axis of the patient corresponds in particular to the axis of rotation of the C-arm, only particular acquisition regions of the patient, for example in the head or in the upper torso, are accessible at all. This applies correspondingly for a footside arrangement. Particular acquisition regions are therefore inaccessible for a three-dimensional scan. In this case it is a significant problem that for a full, sufficiently high-quality reconstruction from the projection images it is necessary to cover a projection angle range, in particular in a reference plane via a (partial) circular path, of more than 180°. In a notional lateral arrangement of the C-arm, if it thus in other words encompasses the patient or the latter's longitudinal axis, the attempt to cover such a large projection angle range would however result in collisions with the patient table, other components of the X-ray device and/or even with the patient him/herself.

DE 199 33 229 A1 discloses by way of example an X-ray device with an X-ray examination stand, which has a base and an arm, the first end of which is arranged such that it can rotate about a first shaft arranged in the base and the second end of which is connected to a mount, in which a curved support is displaceably arranged. One end of the support is provided with an X-ray tube and the other end with a receptor, which are directed at one another. In this case the mount of the support should be connected to the arm such that it can rotate via a second shaft, wherein the first shaft for the base or for the arm and the second shaft for the arm or for the mount are directed such that their imaginary shaft extensions and the central beam of the X-ray tube or of the receptor intersect a common point in all positions of the arm and of the support. In this way individual, desired specific positions of the support corresponding to a C-arm can be assumed, wherein it should there specifically be possible to bring the support from a headside position into a vertical sideways position and/or into a lateral position while retaining an imaginary isocenter. In this case the doctor should also have very good access to the patient. Nevertheless, even in the case of an X-ray device such as this an acquisition trajectory along a circular path in a reference plane which is perpendicular to the longitudinal direction of the patient is not possible with a laterally arranged C-arm, without the risk of collisions with other components and/or the patient.

To solve this problem, telescopic solutions have already been employed in the prior art which are structurally highly complex and are extremely expensive to implement.

SUMMARY

The use of open profiles, in which for example rollers on which the C-arm is guided are exposed during the examination has also been proposed. However, these are disadvantageous, since then the mechanism of the X-ray device would be freely accessibly during the examination. This is undesirable, in particular in environments in which medical interventions and/or examinations are to be performed, for reasons of hygiene, ease of cleaning and vulnerability of the mechanism.

One or more example embodiments of the present enables lateral 3D scans too, free from collisions, with a simple structural configuration and a compactly-sized X-ray device.

This is achieved by a computer-implemented method for operating an X-ray device for acquiring projection images of an acquisition region of a patient. The X-ray device may include a stand, a support arm, a mount and a C-arm, on which are arranged, opposing one another, an X-ray generator and an X-ray detector. The support arm may be coupled to the stand at one end such that it can rotate about a first axis of rotation for the creation of a first degree of freedom of movement and the mount is coupled to the support arm at another end such that it can rotate about a second axis of rotation for the creation of a second degree of freedom of movement, so that the first axis of rotation, the second axis of rotation and a central beam of the X-ray generator intersect at one point in all positions of the support arm and of the mount, and wherein the C-arm is further displaceably mounted in a guide of the mount for the creation of a third degree of freedom of movement. Each of the degrees of freedom of movement may be assigned an actuator that can be activated by a control device of the X-ray device. The method may include acquiring the projection images along a lateral trajectory, three-dimensional with respect to a reference plane, of the X-ray generator encompassing the patient laterally with respect to a longitudinal direction of the patient, for a coverage of a projection angle range of at least 200° with respect to the reference plane. The lateral trajectory may use all three degrees of freedom of movement such that the C-arm is positioned laterally next to the patient along the entire lateral trajectory with respect to the longitudinal direction of the patient or of a patient couch on which the patient is positioned. This is also achieved by an X-ray device that includes an X-ray generator, an X-ray detector, a stand, a support arm, a mount, and a C-arm. The X-ray device may be configured to perform the method for acquiring projection images of an acquisition region of a patient. Advantageous embodiments emerge from the subclaims.

BRIEF DESCRIPTION OF THE DRAWINGS

Advantages and details emerge from the exemplary embodiments of the present invention described below and on the basis of the drawings, in which.

DETAILED DESCRIPTION

Figure 1:
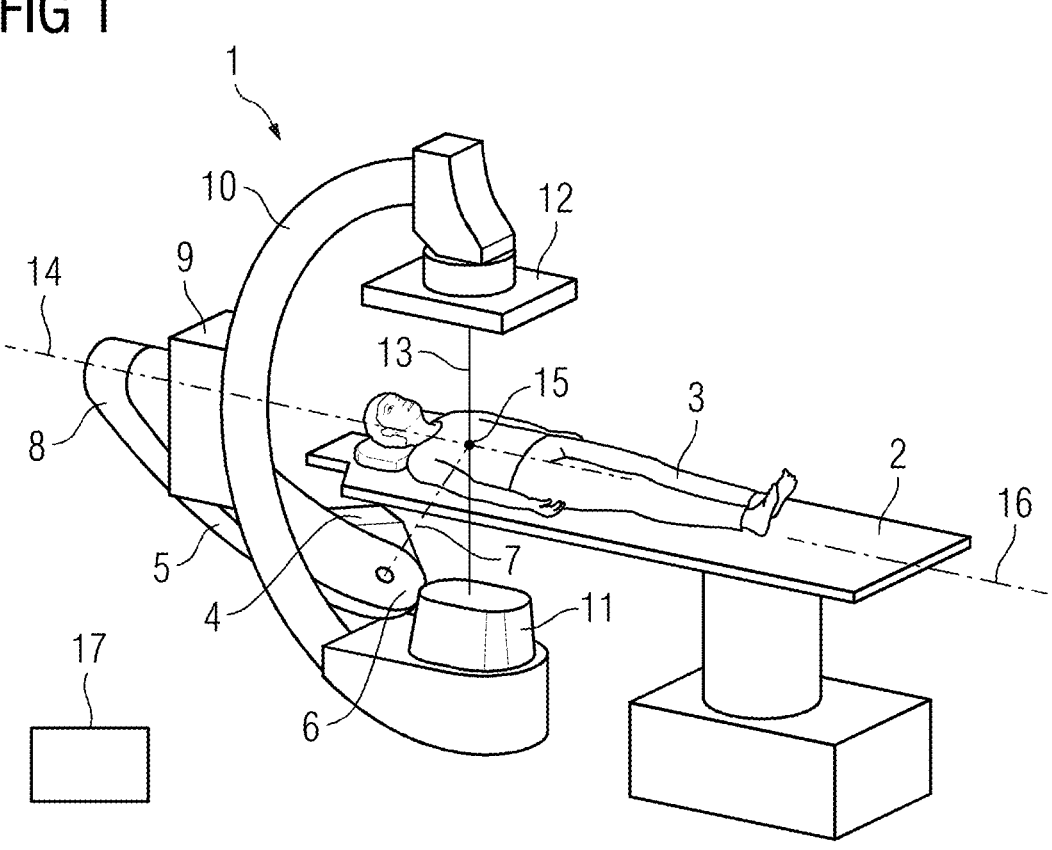
FIG. 1 shows a schematic outline of an inventive X-ray device according to an exemplary embodiment.

In a computer-implemented method of the type cited in the introduction it is inventively proposed that the acquisition of the projection images takes place along a three-dimensional lateral trajectory of the X-ray generator, which encompasses the patient laterally with respect to the latter's longitudinal direction, with respect to a reference plane, to cover a projection angle range of at least 200° with respect to the reference plane, wherein the trajectory is implemented by utilizing all three degrees of freedom of movement, such that the C-arm is positioned laterally next to the patient along the entire lateral trajectory with respect to the longitudinal direction of the patient or of a patient couch on which the patient is positioned.

Specifically the control device therefore activates the actuators to implement the lateral trajectory, in particular for the creation of a particular movement sequence with respect to the degrees of freedom of movement, wherein the acquisition of projection images along the lateral trajectory is also controlled by the X-ray device. Then, for example via a reconstruction unit of the control device, a three-dimensional image dataset of the acquisition region can be reconstructed from the projection images. In other words therefore, a lateral, three-dimensional scan of the acquisition region of the patient is enabled.

Whereas normally a three-dimensional scan takes place such that a circular path or partial circular path is used as a trajectory within a reference plane, in particular a reference plane arranged perpendicular to the longitudinal direction of the patient or of the patient table, it has been recognized that in a certain context deviations of the lateral trajectory from the reference plane, therefore a three-dimensionality with respect to the reference plane, can be permitted as an additional degree of freedom, in order to be able to perform a corresponding three-dimensional lateral scan despite a simple and cost-effective configuration of the corresponding X-ray device, without having to fear collisions or compulsorily having to provide the availability of particular settings along the circular path because of the mechanism with which the acquisition array is mounted. In other words, letting the lateral trajectory leave the reference plane allows the travel range to be extended, without having to make complex adjustments to the mechanism, the actuators and the degrees of freedom of movement. It can therefore be said that in accordance with one or more example embodiments of the present invention the three-dimensional lateral trajectory at least does not run completely in a reference plane, but deviates therefrom at least in part.

In this context the projection angle can therefore be understood as the angle of the projection of the central beam onto the reference plane, since the projection angle range to be covered relates precisely to this reference.

Thanks to the lateral positioning of the C-arm with respect to the longitudinal direction of the patient or the patient couch it encompasses the patient laterally, so that the acquisition region lies in the field of view of the acquisition array formed from the X-ray generator and the X-ray detector. In this case encompassing the supine patient in this way from below and above in relation to the longitudinal direction of the patient and/or of the patient couch is also to be understood as lateral positioning.

Because the lateral trajectory deviates from the reference plane it is therefore possible to extend the travel range so that a sufficient projection angle range is covered, such that a three-dimensional image dataset of the acquisition region, which is of sufficient quality, can be reconstructed from the projection images. A further degree of freedom is opened up for trajectory planning, namely leaving the reference plane, in order to achieve sufficient projection angle ranges with respect to the reference plane despite where appropriate the presence of restrictions on the degrees of freedom of movement and/or without the risk of collisions with the patient or a component of the X-ray device.

In this case it can in particular be provided that exclusively the three degrees of freedom of movement cited (rotation about first and second axis of rotation and displacement of the C-arm in the mount) are used to move the C-arm along the lateral trajectory, in that the corresponding actuators are correspondingly activated by the control device. In this case it has been recognized in particular that for example via an X-ray device as described in DE 199 33 229 A1 with the three easily implementable, non-exposed degrees of freedom, high-quality three-dimensional image datasets can therefore be obtained from acquisition regions by permitting a deviation from the reference plane, consequently a three-dimensional lateral trajectory. Whereas the second and the third degree of freedom of movement, rotation about the second axis of rotation and displacement in the mount (known as orbital rotation), are already known in principle in the prior art, it is therefore now in particular possible, thanks to the addition of the support arm and the first degree of freedom of movement, which is easily possible and does not entail the mechanism being exposed, to provide everything necessary to enable a lateral three-dimensional scan of an acquisition region, in that possible shortcomings of the movement mechanism with respect to approachable positions and/or the risk of collisions are circumvented because the lateral trajectory is configured three-dimensionally, and therefore can move out of a reference plane in which it was for example ideally provided as a partial circular path.

It can be said generally that the present implementation advantageously involves neither a complex telescopic principle nor a principle in which the rollers have to leave the guide. Thanks to the clever arrangement of the degrees of freedom of movement a travel angle of more than 180° can be implemented and it is possible to make lateral three-dimensional acquisitions of acquisition regions of a patient. Hitherto this was only possible with an X-ray device of this type in the "headside" position.

It may be mentioned at this point that in the headside position, in other words if the second axis of rotation is at least substantially parallel to the longitudinal direction of the patient and/or of the patient couch, three-dimensional scans can also of course continue to be performed with the X-ray device, as known. In this light it can therefore be said that a further acquisition facility is being added to the X-ray device.

In an expedient development of one or more example embodiments of the present invention it can be provided that the lateral trajectory is determined in an optimization procedure while keeping a safe distance from the patient and/or from components of the X-ray device as a boundary condition, so that it comes to lie as close as possible to an ideal trajectory in the reference plane. This means that, in order to remain as close as possible to an ideal trajectory in the reference plane, the actuators of the degrees of freedom of movement can be operated in alignment with one another such that optimum use is made of the adjustment facilities, without this resulting in collisions, be it with the patient or with components of the X-ray device. In this case use can in principle be made of known optimization techniques which correspondingly take into account the opportunities afforded by the different degrees of freedom of movement. Here, as already mentioned, the ideal trajectory can be a partial circular path, since such partial circular paths are frequently employed in the prior art to cover the projection angle range in the reference plane. On the basis of such partial circular paths a particularly simple reconstruction of a three-dimensional image dataset from the two-dimensional projection images is possible, which in the case of slight deviations from the reference plane can also be applied or transferred, at least in part, to the projection images acquired along the three-dimensional lateral trajectory. The reference plane can be a vertical plane, in particular perpendicular to the longitudinal direction of the patient and/or of the patient couch, therefore in particular a transverse plane, since this represents a medical standard which is also normally used for the headside position.

At least a maximum angular deviation of the central beam from the reference plane, in particular of 10 to 20°, preferably 15°, can also be proposed as a further boundary condition and/or a minimization of said angular deviation as an optimization target. It can therefore be a basic target to keep the angular deviation from the reference plane small. In this way the influence of the three-dimensionality on the reconstruction is kept as small as possible, so that because of the three-dimensionality of the lateral trajectory, artifacts/ interference with image quality can therefore likewise be kept as small as possible. In this case it has been shown that when the angular deviations are restricted to less than 15°, in particular a maximum of 12°, extremely high-quality projection image sets and thus three-dimensional image datasets can be obtained.

In a particularly expedient configuration of the method it can be provided that patient-specific expansion information is determined and is taken into account during the optimization to evaluate the boundary conditions. In the prior art a plurality of possibilities has already been proposed for determining patient sizes or expansions in various substantiation steps. Thus for example patient information can in a simple case merely comprise the position of the patient on the patient couch along with general patient data, such as age, sex, height and/or weight. However, it is particularly advantageous if the patient-specific expansion information is ascertained using a measurement. For example, the surface of the patient can be scanned using a 3D camera, in particular a terahertz camera, and/or a radar device. It is also possible to acquire survey image data via the X-ray device itself and to evaluate it as appropriate. In all these cases it is possible to improve the utilization of clearances occurring for individual patients during trajectory planning and thus where appropriate to come closer to the ideal trajectory, but also at the same time in particular to improve the way in which bulkier patients are protected against collisions.

The projection angle range can preferably be extended beyond a reference angle range to be covered, in particular of 180° plus fan angle, for example 200°, for the acquisition of further projection images to reduce artifacts in a subsequent reconstruction of a three-dimensional image dataset. It has also been shown that artifacts and/or image quality impairments can also be caused by the deviations from the reference plane during the reconstruction, in particular if this is taken over unchanged. Thanks to the acquisition of additional projection images at further projection angles, therefore an extension of the projection angle range compared to a reference angle range, it is possible to provide additional information which helps to significantly reduce such artifacts and/or image quality impairments and to create an excellent image quality of the reconstructed three-dimensional image dataset. In this case it has been shown in examinations that just by a relatively small extension of the projection angle range compared to the reference angle range it is possible to register strong quality gains. For example, it can be provided that the projection angle range is extended by 2 to 10°, in particular 5 to 7°, compared to the reference angle range. Instead of a reference angle range of 200° it is therefore for example conceivable to cover a projection angle range of 206°, which for example with a maximum angular deviation from the reference plane of 12° leads to excellent quality image results.

It can preferably be provided that the first axis of rotation is inclined by 1 to 20°, in particular 18°, compared to the horizontal and/or the travel range about the first axis of rotation is 140 to 160°, in particular 150°, and/or the travel range about the second axis of rotation is 300 to 320°, in particular 310°, and/or the travel range thanks to the displacement of the C-arm in the mount is 140 to 160°, in particular 150°. Examinations have shown that with these values ideal boundary conditions arise for keeping the deviation from the reference plane or from an ideal trajectory for a sustained high imaging quality as low as possible for the lateral scan too. An excellent design is produced with an incline of the first axis of rotation by 18°, travel ranges of 150° for the first axis of rotation and the displacement, and a travel range of 310° for the second axis of rotation.

A development of the method provides that the X-ray detector is mounted such that it can rotate via a further actuator that can be activated by the control device about a detector axis of rotation parallel to the central beam, in particular corresponding thereto, wherein during the lateral trajectory the control device activates the further actuator such that the X-ray detector assumes a predetermined orientation, in particular with opposing longitudinal edges along a longitudinal direction of the patient couch, for all projection images. In this way it can be ensured that even if portions of the trajectory deviate in particular from the reference plane the images have a desired, specified orientation, so that a complex conversion along the lateral trajectory can advantageously be omitted. Furthermore, specifications or standards can be followed.

The acquisition region can for example be an abdominal region and/or a hip region, in particular the patient's liver. As already explained, it is a general design aspiration, in order to keep the X-ray devices compact and minimally disruptive for other people, to configure the C-arm to be rather short, so that the usability of the C-arm for three-dimensional scans in a headside position is frequently restricted to the head and where appropriate portions of the upper torso. This means that with X-ray devices of this type it has hitherto not been possible without great effort and restructuring thereof meaningfully to capture acquisition regions lying therebetween three-dimensionally, for example the liver, the hip region and where appropriate also regions of the thigh, for example when the thighbone has been broken. With the option described here of a lateral three-dimensional scan along the lateral trajectory the possibility is now also opened up for X-ray devices of this type to capture such acquisition regions.

The stand can advantageously be floor-mounted. A floor-standing installation is considerably simpler to implement structurally and makes far fewer demands on the corresponding fastening means; furthermore, less relevant installation space or field of view is taken away. However, in principle it is also conceivable in the context of one or more example embodiments of the present invention to provide a ceiling-mounted stand, but this is less preferable.

Because of the robust, easily implemented mechanism, in particular when only the three cited degrees of freedom are used, relatively high movement speeds of the acquisition array, in particular of the X-ray generator, along the lateral trajectory are possible in a stable manner. For example, the movement along the lateral trajectory can take place at an angular speed of at least 40° per second, in particular at least 50° per second. In this case the angular speed can in particular also relate to the projection angle in the reference plane. This makes extremely fast acquisitions possible, since the projection angle range is scanned in full in a few seconds. Thus the vulnerability to movements is also significantly reduced.

In this connection especially it should be noted that the inventive procedure can also be employed for image acquisition techniques that use contrast agents, since sufficiently fast three-dimensional lateral scans are possible using the three-dimensional lateral trajectory, deviating at least partially from the reference plane. This applies in particular for digital subtraction angiography (DSA), in which it can particularly advantageously be provided that projection images are acquired during two successive passes, taking place in reverse directions, of the lateral trajectory, in particular as mask projection images prior to a contrast agent reaching the acquisition region and in the second pass of the lateral trajectory as filling images after the arrival of the contrast agent in the acquisition region. Specifically, it can for example be provided that initially the C-arm and thus the acquisition array consisting of an X-ray generator and an X-ray detector is brought into a starting position corresponding to one of the end positions of the lateral trajectory. Initially the first pass of the lateral trajectory to the other end position of the lateral trajectory for the acquisition of the mask projection images (mask run) takes place from there, in particular coordinated in time with a pattern of contrast agent accumulation in the acquisition region. The second pass of the lateral trajectory back to the end position of the lateral trajectory used as a starting position then takes place from this other end position of the lateral trajectory, wherein then the filling projection images can be acquired (filling run). The C-arm can then for example be moved back again from the starting position into a rest position.

Besides one or more example embodiments of the present invention also relates to an X-ray device, having a stand, a support arm, a mount and a C-arm, on which are arranged an X-ray generator and an X-ray detector opposing one another, wherein the support arm is coupled to the stand at one end such that it can rotate about a first axis of rotation for the creation of a first degree of freedom of movement and the mount is coupled to the support arm at the other end such that it can rotate about a second axis of rotation for the creation of a second degree of freedom of movement, so that the first and the second axis of rotation as well as a central beam of the X-ray generator intersect at one point in all positions of the support arm and of the mount, and wherein the C-arm is further displaceably mounted in a guide of the mount for the creation of a third degree of freedom of movement, wherein each of the degrees of freedom of movement is assigned an actuator that can be activated by a control device of the X-ray device, said X-ray device being distinguished in that the control device is designed for the performance of the inventive method. All explanations with respect to the inventive method can be transferred analogously to the inventive X-ray device, with which therefore likewise the aforementioned advantages can be obtained.

The control device can comprise at least one processor and at least one storage means. Using hardware and/or software of the control device it is possible to create functional units in order to perform various steps of the inventive method. Thus the control device can for example have a trajectory unit for activating the actuators for the performance of acquisition trajectories, in particular the lateral trajectory, as well as an acquisition unit which controls the acquisition operation of the X-ray generator and of the X-ray detector, in particular the acquisition of the projection images. In a reconstruction unit the two-dimensional projection images can be used to reconstruct a three-dimensional image dataset. The control device can also comprise further functional units for the implementation of developments of the inventive method, for example a trajectory planning unit for the performance of an optimization procedure for planning the lateral trajectory.

FIG. 1 shows a schematic outline of an inventive X-ray device 1. This initially comprises a patient couch 2, on which a patient 3 is indicated. The patient couch is part of a patient table, which for example can be designed to be fixed to the floor.

A stand 4 on which a support arm 5 is arranged at a first end 6 so as to rotate about an axis of rotation 7 can likewise be attached to the floor. The second end 8 of the support arm 5 is connected to a mount 9, in which a C-arm is displaceably mounted. The C-arm 10 has an X-ray generator 11 and opposing this an X-ray detector 12, wherein a central beam 13 of this acquisition array is likewise shown. The mount 9 is mounted on the second end 8 of the support arm 5 so as to rotate about a second axis of rotation 14. The first axis of rotation 7, the second axis of rotation 14 and the central beam 13 can be seen to intersect at a common point 15, which applies for all positions/locations of the corresponding components. Regardless of the specific setting of the rotation of the support arm 5, of the rotation of the mount 9 and of the displacement of the C-arm 10, the location of the point 15 in space is therefore always the same.

The first axis of rotation 7 is in this case inclined by 18° compared to the horizontal. The travel ranges with respect to the first axis of rotation 7 and the displacement of the C-arm 10 in the mount 9 are 150° and the travel range about the second axis of rotation is 310°.

FIG. 1 shows the C-arm 10 in what is known as a headside position. Here the patient 3 is mounted on the patient couch 2 such that said patient's longitudinal direction runs in parallel to the longitudinal direction 16 of the patient couch 2. In the headside position in FIG. 1 the second axis of rotation 14 now runs at least substantially in parallel to this longitudinal direction 16. Thus the C-arm 10 can be rotated about the patient 3, encompassing the latter from the head, such that the X-ray generator 11 moves along a circular path in a plane perpendicular to the longitudinal direction 16. However, the C-arm 10 is designed to be short, so that, from the headside position, acquisition regions in the abdomen, hip region and at least partially thigh region cannot be scanned in this manner.

To control the operation of the X-ray device 1 the latter has a control device 17, with which not only a headside scan as just described can be performed, but the control device 17 is also designed to perform the inventive method, which permits a lateral three-dimensional scan using the three degrees of freedom of movement described (rotation about a first axis of rotation 7, rotation about a second axis of rotation 14 and displacement in the mount 9, which has a corresponding guide).

It should again be noted at this point that all three discussed degrees of freedom of movement of the C-arm 10 are assigned corresponding actuators, not shown in greater detail in FIG. 1 for reasons of clarity, which can be activated via the control device 17. This means, both as regards the rotation about the first axis of rotation 7 and the second axis of rotation 14 and also as regards the displacement of the C-arm 10 in the guide of the mount 9, that in each case actuators are present that can be activated. A trajectory of the X-ray generator 11 can in particular be described by the pattern of control signals for the actuators (and thus corresponding partial movement sequences in the degrees of freedom of movement). As a further movement option, which can be activated via the control device 17, the X-ray detector 12 designed here as a flatbed detector can be rotated about an axis of rotation corresponding to the central beam 13.

Figure 2:
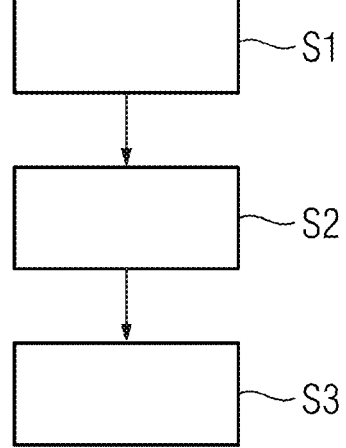
FIG. 2 shows a flow chart of an exemplary embodiment of the inventive method.

FIG. 2 shows a flow chart of an exemplary embodiment of the inventive method. In this case a lateral trajectory is ascertained, which, in order that it can be implemented without collision and with the movement clearances of the degrees of freedom of movement, uses an additional degree of freedom, namely the possibility of deviating from a here vertical reference plane oriented perpendicular to the longitudinal direction 16, which means leaving said reference plane and thus being three-dimensional.

Specifically, in a step S1 the lateral trajectory is initially ascertained in an optimization procedure. The optimization target in this case is to obtain a lateral trajectory that lies as close as possible to the ideal trajectory in the reference plane, here a partial circular path in a vertical plane perpendicular to the longitudinal direction 16, as could be implemented for example in the headside position by simple rotation about the second axis of rotation 14, cf. FIG. 1. A further optimization target may in this case be to permit as small angular deviations as possible from the reference plane, for example with respect to the point 15. Required boundary conditions, besides the specified movement clearances of the individual degrees of freedom of movement, therefore what is mechanically possible, are that no collision with the patient 3 or a component of the X-ray device 1 takes place, in particular therefore not with the patient couch 2 or the table stands supporting it. Further boundary conditions may include that a particular angle of deviation from the reference plane should not be exceeded. The lateral trajectory is ascertained in the optimization procedure so that a particular projection angle range that is desired is covered, wherein the projection angle range relates to the reference plane, therefore the projection of the central beam into said reference plane. The projection angle range is in this case expediently selected to be larger than the minimum required for the full reconstruction, in particular therefore larger than 180° plus the fan angle. With a fan angle of 20°, 200° would in principle be sufficient for a full reconstruction covered by projection images, but there is a deviation here from the reference plane, so that additional projection information is useful in order to reduce artifacts and image quality impairments as much as possible. In the present case by way of example a projection angle range of 206°, extended compared to the reference angle range of 200°, is covered by the lateral trajectory.

In the present exemplary embodiment the lateral trajectory is ascertained patient-specifically, so that patient-specific expansion information is used for the evaluation of the boundary condition, and can be based on existing patient data such as height, sex, age and weight, but has preferably been measured via a measuring device, for example a 3D camera, in particular a terahertz camera, and/or a radar device.

Then in a step S2, via a trajectory unit of the control device, the particular lateral trajectory is started by activation of the corresponding actuators. At the same time, controlled via an acquisition unit of the control device, projection images are acquired using different projection geometries, therefore projection angles, via the acquisition array formed from the X-ray generator 11 and the X-ray detector 12. The acquisition region can in this case in particular be an abdominal region and/or a hip region, since these cannot be scanned three-dimensionally in the headside position, as described. The speed at which the X-ray generator 11 moves along the lateral trajectory and which hence also corresponds to the speed of the X-ray detector 12, can be at least 40° per second in relation to the projection angle, in particular at least 50° per second in relation to the projection angle. Thus an extremely fast measurement that has little susceptibility to movement is possible.

In a step S3 the projection images are then evaluated, in order to use a reconstruction method to reconstruct a three-dimensional image dataset of the acquisition region. A filtered backprojection method can for example be used as a reconstruction method. The three-dimensional image dataset reconstructed in this way can for example be displayed to a user, stored, or else also further evaluated.

It should again be noted at this point that in principle a two-fold pass of the lateral trajectory can also take place, for example in a bidirectional manner, in order to be able to acquire both mask projection images and filling projection images when using a contrast agent, in particular during an examination of the digital subtraction angiography.

In step S2 the control device 17 can also be designed to activate an actuator assigned to the torsion of the X-ray detector 12, in order, even when deviating from the reference plane, to adjust the orientation of the detector so that there is a specified orientation, for example with longitudinal edges corresponding to the longitudinal direction 16.

Figure 3:
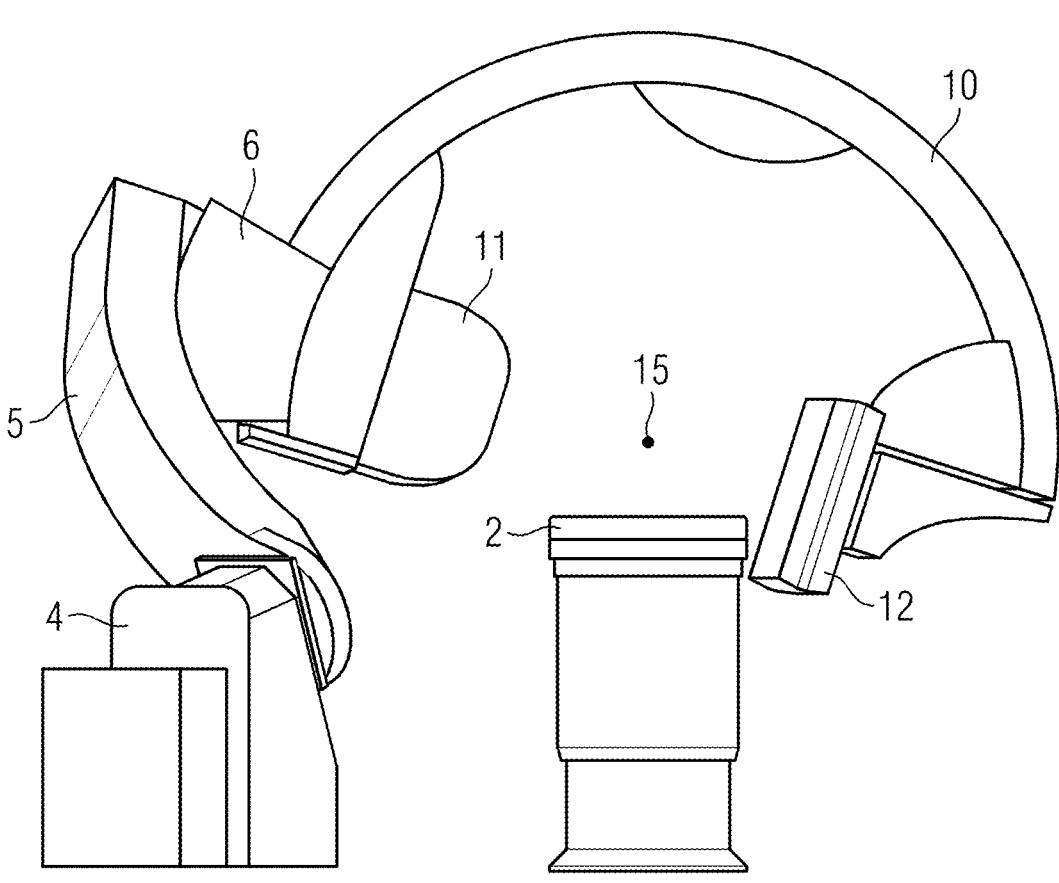
FIG. 3 to FIG. 6 show different positions of the X-ray device during an exemplary lateral trajectory.
Figure 4:
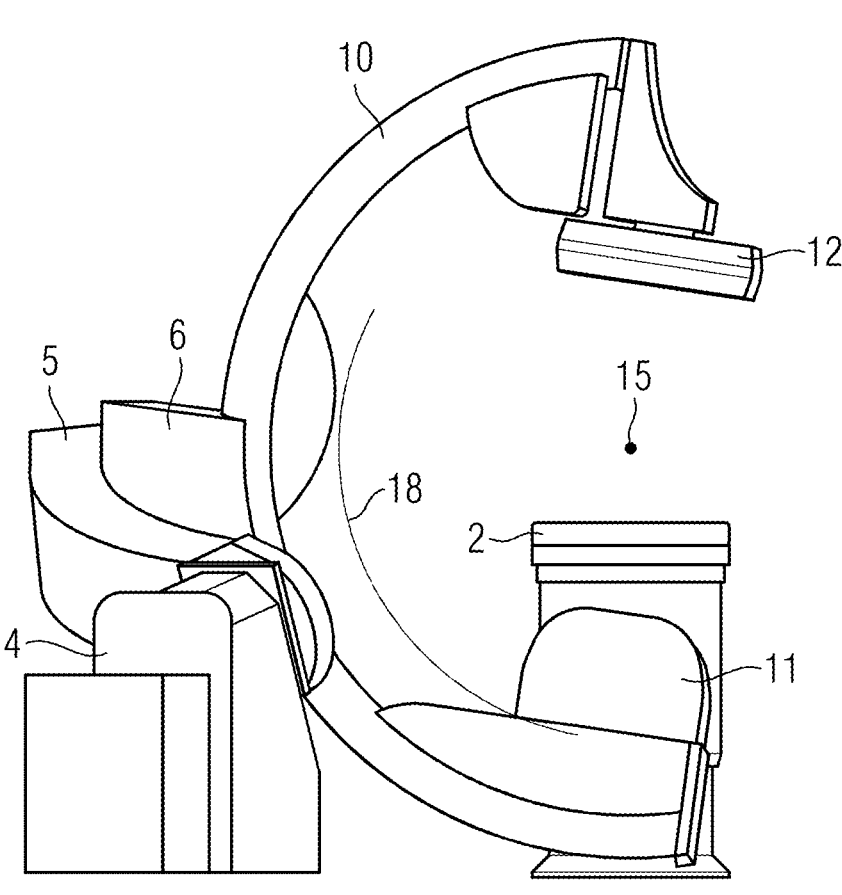
Figure 5:
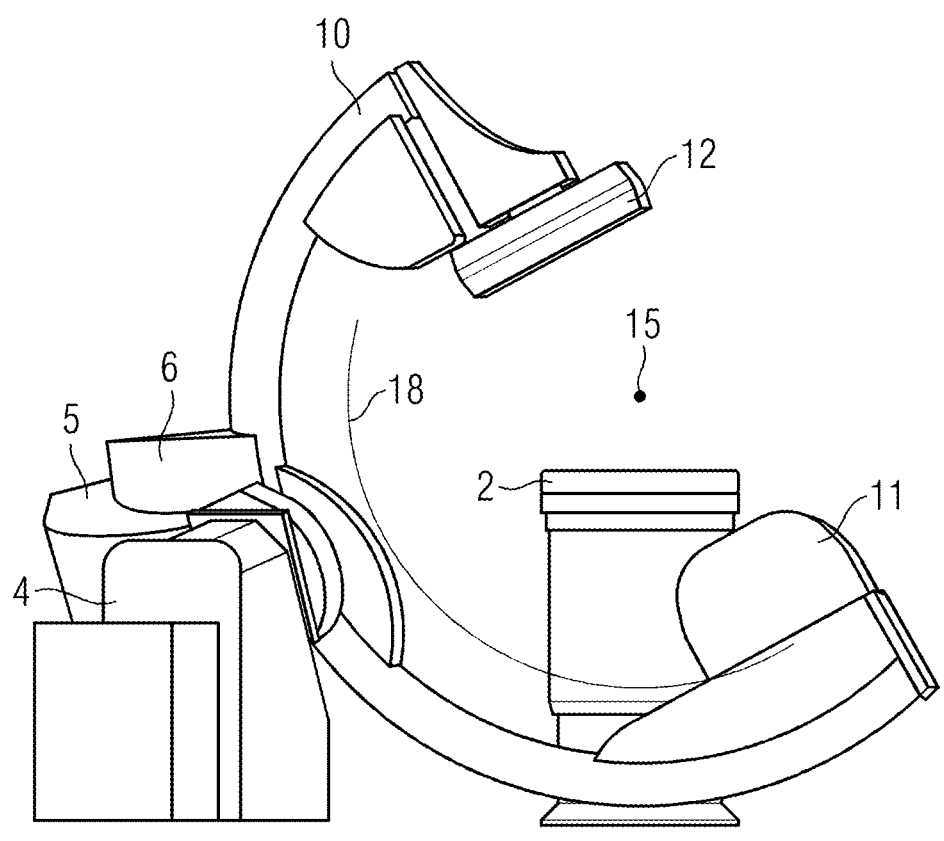
Figure 6:
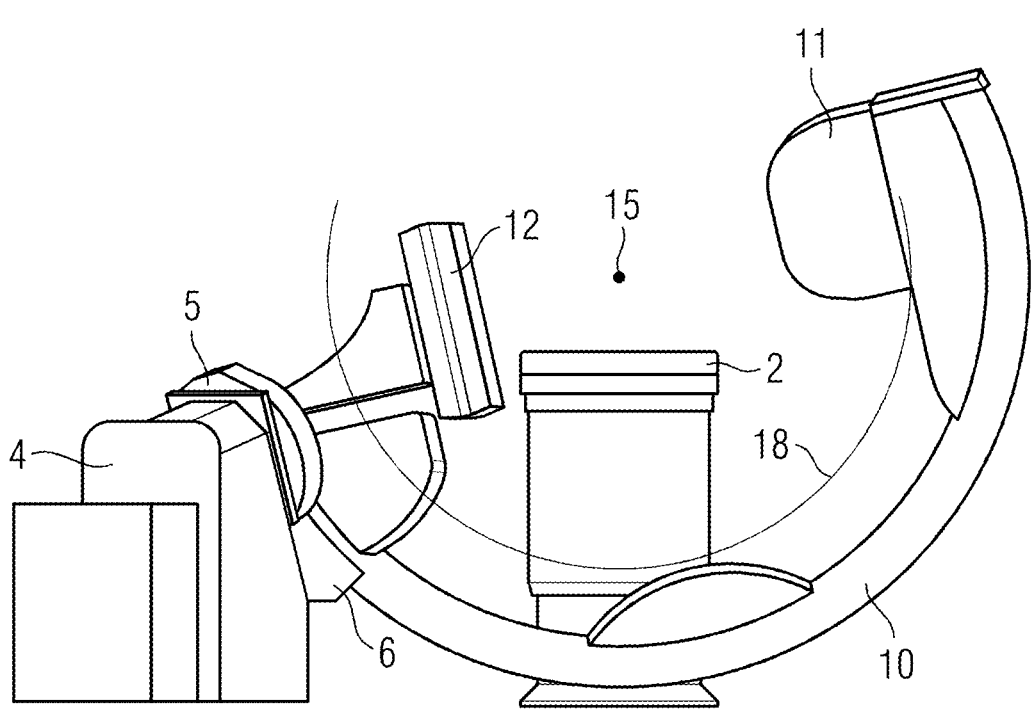

FIGS. 3 to 6 show by way of example a possible implementation of the lateral trajectory in the form of four snapshots, wherein FIG. 3 shows the starting point as a first end position of the lateral trajectory and FIG. 6 shows the end point as a second end position of the lateral trajectory. FIGS. 4 and 5 show intermediate states. The lateral trajectory 18 which develops and is slowly completed is correspondingly indicated.

Figure 7:
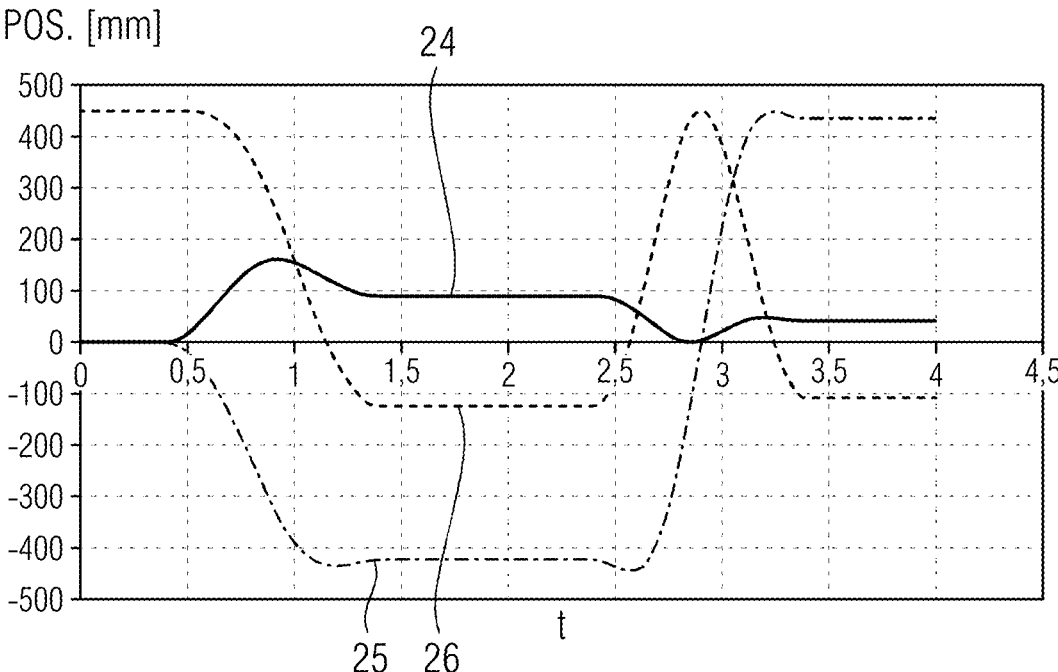
FIG. 7 shows the progression of the position of the X-ray detector during the lateral trajectory in FIGS. 3 to 6.

FIG. 7 shows the movement of the X-ray detector 12 as an absolute position (Pos.) along the axes of a right-angled coordinate system, which has its origin in the point 15, against time (t) during the lateral trajectory in FIGS. 3 to 6. In this case the curve 24 relates to a coordinate corresponding to the longitudinal direction 16, the curves 25 and 26 in each case to a horizontal direction perpendicular thereto and to a vertical direction perpendicular thereto. The curve 24 clearly shows the deviation from the reference plane, whereas the curves 24 and 25 illustrate the coverage of the projection angle range, but also show the deviation from a perfect circular path/partial circular path.

Figure 8:
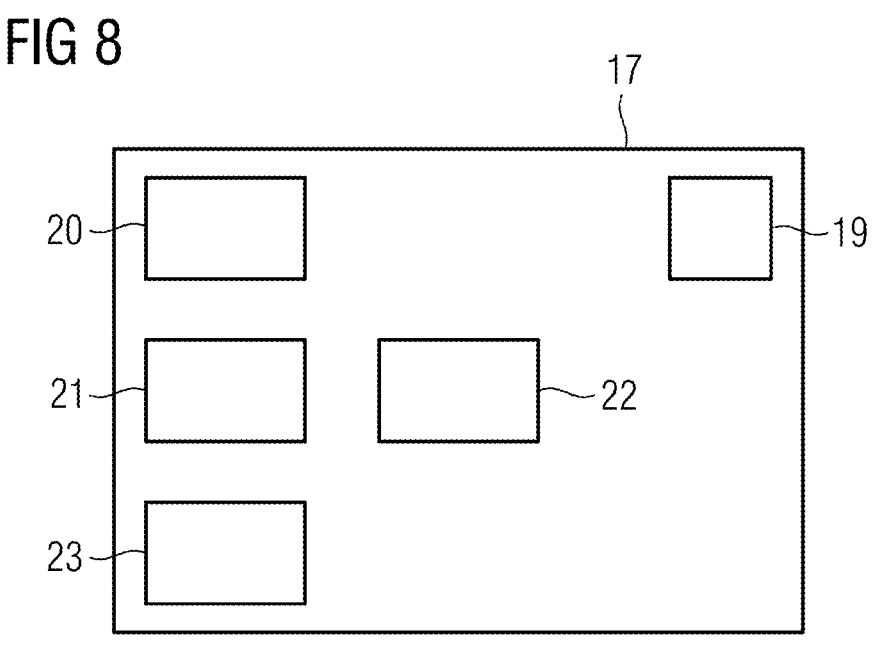
FIG. 8 shows the functional structure of a control device of the X-ray device according to an exemplary embodiment.

FIG. 8 shows the functional structure of the control device 17 designed for the performance of the inventive method in greater detail. This initially has a storage means 19, in which interim and final results can be stored, for example the projection images and the three-dimensional image dataset.

The lateral trajectory is ascertained in a trajectory planning unit 20 in accordance with step S1. A trajectory unit 21 for activating the actuators and an acquisition unit 22 for activating the acquisition array cooperate for the implementation of step S2. A reconstruction unit 23 can be used to reconstruct three-dimensional image datasets from the projection images in accordance with step S3.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the invention has been illustrated and described in greater detail by the preferred exemplary embodiment, the invention is not restricted by the disclosed examples and other variations can be derived therefrom by the person skilled in the art, without departing from the scope of protection of the invention.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

The invention claimed is:

1. A computer-implemented method for operating an X-ray device for acquiring projection images of an acquisition region of a patient, the method comprising:
   acquiring the projection images along a lateral trajectory, three-dimensional with respect to a reference plane, of an X-ray generator encompassing the patient laterally with respect to a longitudinal direction of the patient, for a coverage of a projection angle range of at least 200° with respect to the reference plane, wherein
   the X-ray device includes a stand, a support arm, a mount and a C-arm, on which are arranged, opposing one another, the X-ray generator and an X-ray detector,
   the support arm is coupled to the stand at one end such that it can rotate about a first axis of rotation for creation of a first degree of freedom of movement and the mount is coupled to the support arm at another end such that it can rotate about a second axis of rotation for creation of a second degree of freedom of movement, so that the first axis of rotation, the second axis of rotation and a central beam of the X-ray generator intersect at one point in all positions of the support arm and of the mount,
   the C-arm is further displaceably mounted in a guide of the mount for creation of a third degree of freedom of movement,
   each of the first degree of freedom of movement, the second degree of freedom of movement, and the third degree of freedom of movement is assigned an actuator that can be activated by a control device of the X-ray device, and
   the lateral trajectory uses all three degrees of freedom of movement such that the C-arm is positioned laterally next to the patient along an entire lateral trajectory with respect to the longitudinal direction of the patient or of a patient couch on which the patient is positioned.

2. The method of claim 1, furthering comprising:
   determining the lateral trajectory using at least one of,
      an optimization procedure while maintaining a safe distance from the patient, or
      components of the X-ray device as a boundary condition, so that they come to lie as close as possible to an ideal trajectory in the reference plane.

3. The method of claim 2, wherein at least one of the ideal trajectory is a partial circular path or a vertical plane is used as the reference plane.

4. The method of claim 2, wherein at least one of,
   at least a maximum angular deviation of the central beam from the reference plane is specified as a further boundary condition, the maximum angular deviation being from 10 to 20°, or
   a minimum angular deviation is specified as an optimization target.

5. The method of claim 2, further comprising:
   determining patient-specific expansion information, wherein the optimization procedure is based on the patient-specific expansion information.

6. The method of claim 1, further comprising:

extending the projection angle range for an acquisition of further projection images for a reduction of artifacts in a subsequent reconstruction beyond a reference angle range to be covered.

7. The method of claim 6, wherein the extending extends the projection angle range compared to the reference angle range by 2 to 10°.

8. The method of claim 1, wherein at least one of the first axis of rotation is inclined by 1 to 20° compared to a horizontal, a travel range about the first axis of rotation is 140 to 160°, the travel range about the second axis of rotation is 300 to 320°, in particular 310°, or the travel range due to displacement of the C-arm in the mount is 140 to 160°.

9. The method of claim 1, wherein the X-ray detector is mounted such that it can rotate via a further actuator, which can be activated by the control device, about a detector axis of rotation parallel to the central beam, in particular corresponding thereto, wherein during the lateral trajectory the control device activates the further actuator such that the X-ray detector assumes a specified orientation for the projection images.

10. The method of claim 1, wherein the acquisition region is at least one of an abdominal region or a hip region.

11. The method of claim 1, wherein the stand is floor-mounted.

12. The method of claim 1, wherein the movement along the lateral trajectory takes place at a speed of at least 40° per second.

13. An X-ray device comprising:

an X-ray generator;

an X-ray detector;

a stand;

a support arm;

a mount; and a C-arm, the stand, the support arm, the mount and the C-arm-C are being arranged on, opposing one another, the X-ray generator and the X-ray detector, wherein the support arm is coupled to the stand at one end such that it can rotate about a first axis of rotation for creation of a first degree of freedom of movement and the mount is coupled to the support arm at another end such that it can rotate about a second axis of rotation for creation of a second degree of freedom of movement, such that the first axis of rotation, the second axis of rotation and a central beam of the X-ray generator intersect at one point in all positions of the support arm and of the mount, and wherein the C-arm is further displaceably mounted in a guide of the mount for creation of a third degree of freedom, wherein each of the degrees of freedom is assigned an actuator that can be activated by a control device of the X-ray device, wherein the control device is configured to cause the X-ray device to perform the method of claim 1.

14. The method of claim 3, wherein at least one of, at least a maximum angular deviation of the central beam from the reference plane is specified as a further boundary condition, the maximum angular deviation being from 10 to 20°, or a minimum angular deviation is specified as an optimization target.

15. The method of claim 3, further comprising:

determining patient-specific expansion information, wherein the optimization procedure is based on the patient-specific expansion information.

16. The method of claim 15, further comprising:

extending the projection angle range for an acquisition of further projection images for a reduction of artifacts in a subsequent reconstruction beyond a reference angle range to be covered.

17. The method of claim 16, wherein the extending extends the projection angle range compared to the reference angle range by 2 to 10°.

18. The method of claim 3, wherein at least one of the first axis of rotation is inclined by 1 to 20° compared to a horizontal, a travel range about the first axis of rotation is 140 to 160°, the travel range about the second axis of rotation is 300 to 320°, in particular 310°, or the travel range due to displacement of the C-arm in the mount is 140 to 160°.

* * * * *